US00PP16756P3

(12) United States Plant Patent
NeSmith et al.

(10) Patent No.: US PP16,756 P3
(45) Date of Patent: Jul. 4, 2006

(54) SOUTHERN HIGHBUSH BLUEBERRY PLANT NAMED 'PALMETTO'

(50) Latin Name: ***Vaccinium* sp.**
Varietal Denomination: Palmetto

(75) Inventors: D. Scott NeSmith, Molena, GA (US); Arlen D. Draper, Payson, AZ (US)

(73) Assignee: The University of Georgia Research Foundation, Athens, GA (US)

( * ) Notice: Subject to any disclaimer, the term of this patent is extended or adjusted under 35 U.S.C. 154(b) by 0 days.

(21) Appl. No.: 10/909,650

(22) Filed: Aug. 2, 2004

(65) Prior Publication Data

US 2006/0070150 P1 Mar. 30, 2006

(51) Int. Cl.
*A01H 5/00* (2006.01)

(52) U.S. Cl. ..... Plt./157
(58) Field of Classification Search ..... Plt./157
See application file for complete search history.

(56) References Cited

U.S. PATENT DOCUMENTS

PP10,675 P 11/1998 Lyrene

OTHER PUBLICATIONS http://www.gsdc.com/PALMETTO.html.*
Nesmith D Scott et al. Palmetto Southern Highbush Blueberry Hortscience 39 (7): pp. 1774–1775 Dec. 2004.*
NeSmith D Scott et al. Palmetto: A new southern highbush blueberry cultivar Hortscience 39 (3): pp. 649–650 Jun. 2004.*
U.S. Appl. No. 10/255,211.
U.S. Appl. No. 10/646,660.
'Austin'.
'Black Giant'.
'Brightwell'.
'Clara'.
'Ethel'.
Georgiagem.
'Menditoo'.
'Myers'.
'Powderblue'.
'Premier'.
'Tifblue'.

* cited by examiner

*Primary Examiner*—Kent Bell
*Assistant Examiner*—W. C. Haas
(74) *Attorney, Agent, or Firm*—MacCord Mason PLLC

(57) ABSTRACT

The most distinctive feature of the southern highbush blueberry, 'Palmetto', is its combination of early ripening, favorable commercial fruit attributes, concentrated ripening, good yield and excellent plant vigor suitable for berry production in Georgia.

1 Drawing Sheet

STATEMENT AS TO RIGHTS TO INVENTIONS MADE UNDER FEDERALLY-SPONSORED RESEARCH AND DEVELOPMENT

The invention was made in part with Federal funds pursuant to the Hatch Act.

Botanical designation: *Vaccinium* sp. Variety denomination: 'Palmetto'.

BACKGROUND OF THE INVENTION

1. Field of the Invention

The fruit of the plant is primarily used as fresh fruit for shipping. Also suitable for customer-pick and processing markets.

2. Description of Relevant Prior Art

'Palmetto' was selected as a single plant in 1985 at the Coastal Plain Experiment Station in Tifton, Ga. from a cross of 'US-158'×'TH-157'. 'US-158' is an $F_1$ hybrid of 'FL-4-B' (*V. darrowi*) and a highbush blueberry (*V. corymbosum*). 'TH-157' was derived from a cross of highbush blueberry and 'FL 63-4', a complex hybrid of complex parentage. 'Palmetto' is a hybrid containing mostly *V. cornymbosum* with a small amount of *V. darrowi.* None of the lines used to produce this selection are patented. 'Palmetto' has been tested in a planting at Alapaha, Ga. since 1992, and was planted in other locations beginning in 2001. From a comparison with the popular variety 'Star' (U.S. Plant Pat. No. 10,675) at 3 locations in Georgia and one location in Mississippi, 'Palmetto' appears to be as widely adapted as 'Star'.

The new variety has been asexually propagated on many occasions since 1985 by softwood cuttings. It roots readily from softwood cuttings and in all cases the clones propagated from cuttings have maintained the vegetative and fruit characteristics of the original selection.

'Palmetto' has been primarily compared with the standard southern highbush cultivars 'Georgiagem' (non patented), and 'Sharpblue' (non patented). Georgia producers have found it difficult to grow 'Georgiagem' and need earlier ripening cultivars. 'Sharpblue' also has not been widely grown by Georgia growers due to early flowering and protracted ripening. Over a 5 year period 'Georgiagem' yielded no fruit during the first week of May, whereas 'Palmetto' yielded on average more than 35% of its fruit during that time period. When the first 2 weeks of May are considered, 'Palmetto' ripened on average more than 75% of its fruit during that time, compared to only 38% and 51% for 'Georgiagem' and 'Sharpblue' respectively. 'Palmetto' yields overall were 37% greater than 'Georgiagem', but not significantly different from 'Sharpblue' over the 5 year period.

Average ratings of berry attributes and plant vigor for these 3 cultivars grown at Alapaha, Ga. over a 6 year period showed that 'Palmetto' exceeded the other cultivars with a value rating of 8.8 on a 1 to 10 scale compared to 7.0 and 6.8 with respect to plant vigor, and berry scar was superior with a rating of 8.5 compared to 7.0 and 7.8 for the other cultivars. 'Palmetto' was generally similar to the other cultivars for other berry attributes, except for berry size, which was smaller, but commercially acceptable. Thus, 'Palmetto' has good to excellent fruit quality, and outstanding plant vigor.

Flowering and ripening times are important for growers. Growers want fruit ripening to be early enough to offer a high value for the fruit, but flowering late enough to escape frost damage. Over a 6 year period, 'Palmetto' was in the middle of a group of cultivars grown at Alapaha, Ga. with respect to flowering date, yet, generally ripened the earliest.

To date, little or no southern highbush cultivars grown in Georgia are machine harvested. Data from a 1999 experiment comparing firmness of hand harvested and machine harvested 'Palmetto' and 'Georgiagem' showed that 'Georgiagem' had the typical response of a great loss in firmness of berries due to mechanical harvesting, whereas, 'Palmetto' appeared to remain firm when mechanically harvested.

SUMMARY OF THE INVENTION

Descriptions and specifications of a new and distinct southern highbush blueberry named 'Palmetto' which originated from seed produced by a hand-pollinated cross of 'US-158' and 'TH-157' is provided. The new 'Palmetto' variety can be distinguished from the southern highbush varieties currently available for blueberry production in Georgia by its short ripening period, its overall higher yield, its greater plant vigor, and its high quality fruit suitable for mechanical harvesting.

BRIEF DESCRIPTION OF PHOTOGRAPH

The accompanying photograph shows typical specimens of the fruit and leaf of 'Palmetto' in color as nearly true as it is reasonably possible to make a color illustration of this character. The plant shown in the photograph is a 4 year old plant grown in Ware County, Georgia.

BOTANICAL DESCRIPTION OF THE PLANT

The following is a detailed description of the botanical and pomological characteristics of the subject blueberry clone. Where dimensions, sizes, colors, and other characteristics are given, it is to be understood that such characteristics are approximations and averages set forth as accurately as practicable. Color data are presented in Royal Horticultural Society Colour Chart designations. The descriptions reported herein are largely from 10 year old specimen plants grown in Alapaha, Ga. without supplemental irrigation.

Plant:

*Size.*—1.5 m to 2.0 m tall; canopy width 1.8 m after 10 years without pruning.

*Growth habit.*—Spreading growth habit. Narrow crowns with 1 or 2 main stems at soil surface that branch beginning 15 cm to 20 cm above the soil. There is little or no tendency for suckering.

*Growth.*—Medium-to-high vigor; moderate cane growth.

*Productivity.*—Medium, averaging 6 lbs. per plant each year for 5 year average without irrigation. More than 75% of the fruit ripen in the first 2 weeks.

*Cold hardiness.*—Similar to other southern highbush cultivars such as 'Sharpblue' and 'Georgiagem'.

*Chilling requirement.*—Plants require 350 to 400 hours of temperature at or below 45 F. (7C.) to induce normal leafing and flowering during the spring.

*Leafing.*—Plant does not readily break leaf buds simultaneously with anthesis.

*Canes.*—Canes 3 years or more are 30 mm to 50 mm in diameter, color is typically Grey 201B. 2 year old wood is 5 mm to 10 mm in diameter, color is Yellow Green 146C and current season shoots are 2 to 4 mm in diameter, color is Yellow Green 145A.

*Suckering tendency.*—Little or none.

Foliage:

*Leaf surfaces.*—Nearly smooth.

*Leaf color.*—Healthy mature leaves: top side of leaf color is Yellow-Green 144A, under side of leaf color is Yellow-Green 147D.

*Leaf arrangement.*—Alternate, distichous.

*Leaf shape.*—Elliptic.

*Leaf margins.*—Nearly Entire, slightly crenate near base. Margins slightly fringed (ciliolate).

*Leaf venation.*—Reticulate.

*Leaf apices.*—Acuminate.

*Leaf bases.*—Cuneate to acute.

*Leaf dimensions.*—Length 55 mm to 65 mm; width 25 mm to 35 mm.

*Petioles.*—Small, 2.5 mm to 3.0 mm long. Color Yellow-Green 145C.

Flowers:

*Date of 50% anthesis.*—March 3 in southeast Georgia.

*Flower shape.*—Urceolate.

*Flower bud number.*—Medium.

*Flowers per cluster.*—5 to 8.

*Flower fragrance.*—Yes.

*Corolla color.*—White 155C (open flower); just prior to opening base of corolla has a pink (Red 54C) cast.

*Corolla length.*—8.0 mm to 9.0 mm.

*Corolla width.*—6.0 mm to 7.0 mm.

*Corolla aperture width.*—3.5 mm to 4.0 mm.

*Flower penducle.*—Length to 8.0 mm; Color Yellow-Green 144B.

*Flower pedicle.*—Length 4.0 mm; Color Green 143C.

*Calyx (with sepals).*—Diameter 7.0 mm; color Yellow-Green 144B.

*Stamen.*—Length 7.0 mm; number per flower 10; filament color: Green-White 157A.

*Style.*—Length 9.0 to 9.5 mm; color Yellow-Green 145C.

*Pistil.*—Length 11.0 mm; ovary color (exterior) Yellow-Green 144A.

*Anther.*—Length 4.0 mm; number 10; color Greyed-Orange 172B.

*Pollen.*—Abundance; medium; color Yellow 12D.

The cultivar has a moderate degree of self-compatibility.

Fruit:

*Date of 50% maturity.*—May 9 in southeast Georgia.

*Fruit development period.*—65 to 69 days.

*Berry color.*—With wax Violet-Blue 98C; with wax removed Blue 103A.
*Berry surface wax abundance.*—High.
*Berry flesh color.*—Green-White 157A.
*Berry shape.*—Semi-spherical.
*Berry weight.*—1st harvest 1.3 g to 1.4 g; 2nd harvest 1.0 g to 1.1 g.
*Berry size.*—Height from calyx to scar 12.0 mm; diameter 15.0 mm to 16.0 mm.
*Fruit stem scar.*—Very small, dry, no tearing.
*Berry firmness.*—Good to very good.
*Berry flavor and texture.*—Excellent.
*Seed color.*—Greyed-Orange 165B to 165C.
*Seed weight.*—43.4 mg per 100.
*Seed size.*—1.0 mm to 1.5 mm long.
*Storage quality.*—Very good.
*Suitability for mechanical harvesting.*—Possibly.
*Uses.*—Primarily used as fresh fruit for shipping.

It is claimed:

1. A new and distinct variety of southern highbush blueberry plant, substantially as illustrated and described.

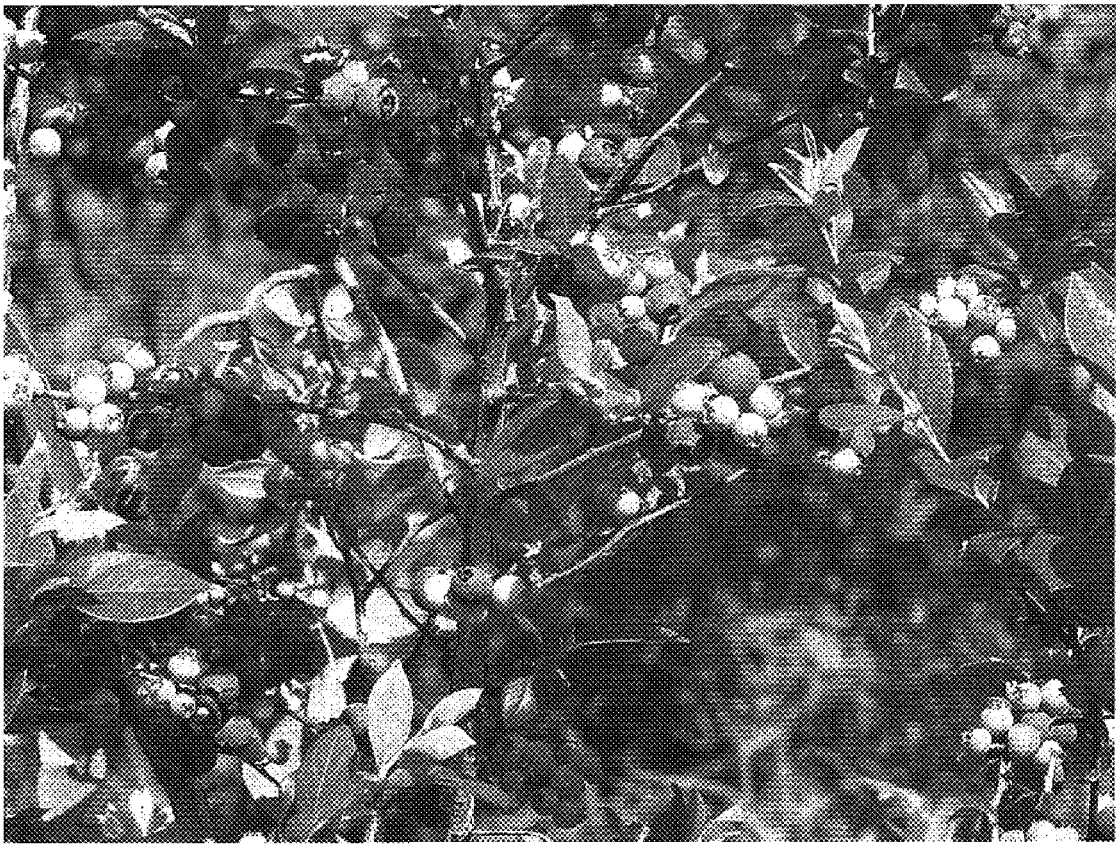

* * * * *